(12) United States Patent
Bonnet et al.

(10) Patent No.: US 8,957,001 B2
(45) Date of Patent: Feb. 17, 2015

(54) PARTICLES COMPRISING A BIOPOLYMER WHICH IS DEGRADABLE UNDER THE EFFECT OF AN ELECTROMAGNETIC WAVE AS EMITTED BY A SOLAR RADIATION

(75) Inventors: Isabelle Bonnet, Lyons (FR); Charlotte De Matteis, Lyons (FR); Eric Perrier, Cotes d'Arey (FR)

(73) Assignee: BASF Beauty Care Solutions France SAS (FR)

( * ) Notice: Subject to any disclaimer, the term of this patent is extended or adjusted under 35 U.S.C. 154(b) by 0 days.

(21) Appl. No.: 13/069,922

(22) Filed: Mar. 23, 2011

(65) Prior Publication Data

US 2012/0053058 A1 Mar. 1, 2012

Related U.S. Application Data

(63) Continuation of application No. 10/346,690, filed on Jan. 15, 2003, now abandoned.

(30) Foreign Application Priority Data

Dec. 24, 2002 (FR) ..................................... 02 16637

(51) Int. Cl.
| | | |
|---|---|---|
| *A01N 25/28* | (2006.01) | |
| *B82Y 5/00* | (2011.01) | |
| *A61K 8/11* | (2006.01) | |
| *A61K 8/60* | (2006.01) | |
| *A61Q 1/06* | (2006.01) | |
| *A61Q 5/02* | (2006.01) | |
| *A61Q 17/04* | (2006.01) | |
| *A61Q 19/00* | (2006.01) | |
| *A61K 8/14* | (2006.01) | |
| *A61K 9/00* | (2006.01) | |

(52) U.S. Cl.
CPC ... *B82Y 5/00* (2013.01); *A61K 8/11* (2013.01); *A61K 8/606* (2013.01); *A61Q 1/06* (2013.01); *A61Q 5/02* (2013.01); *A61Q 17/04* (2013.01); *A61Q 19/00* (2013.01); *A61K 8/14* (2013.01); *A61K 9/0009* (2013.01); *A61K 2800/412* (2013.01); *A61K 2800/413* (2013.01); *A61K 2800/81* (2013.01)
USPC .......................................... 504/359; 424/400

(58) Field of Classification Search
None
See application file for complete search history.

(56) References Cited

U.S. PATENT DOCUMENTS

| 4,766,037 | A | | 8/1988 | Watanabe et al. | |
|---|---|---|---|---|---|
| 5,376,379 | A | * | 12/1994 | Fabre et al. | ................... 424/450 |
| 5,395,620 | A | | 3/1995 | Huc et al. | |
| 5,562,924 | A | | 10/1996 | Perrier et al. | |
| 5,912,016 | A | | 6/1999 | Perrier et al. | |
| 6,348,218 | B1 | | 2/2002 | Hed et al. | |
| 6,548,302 | B1 | * | 4/2003 | Mao et al. | ...................... 435/455 |
| 2002/0064508 | A1 | | 5/2002 | Lyles | |
| 2003/0087436 | A1 | * | 5/2003 | Bayer | ............................ 435/455 |
| 2003/0219384 | A1 | | 11/2003 | Donath et al. | |

FOREIGN PATENT DOCUMENTS

| ES | 2 120 512 | | 11/1998 |
|---|---|---|---|
| ES | 2 155 793 | | 5/2001 |
| JP | 05009107 | | 1/1993 |
| JP | 5009107 | | 1/1993 |
| JP | 8507075 | A | 7/1996 |
| JP | 2001261522 | | 9/2001 |
| JP | 2001261522 | A | 9/2001 |
| JP | 2002506719 | A | 3/2002 |
| WO | 82/00943 | | 4/1982 |
| WO | WO 82/00943 | * | 4/1982 |
| WO | 9418954 | A1 | 1/1994 |
| WO | WO 96/01617 | | 1/1996 |
| WO | WO 99/60167 | | 11/1999 |
| WO | WO 0139744 | | 6/2001 |

OTHER PUBLICATIONS

Bottiglieri, P. Derwent Document Identifier: CH678489A, "Cosmetic comps. contg. placental extract, thymus", Sep. 30, 1991.*
Barnhart, B.J. et al., "Radiation Sensitivity of *Haemophilus influenzae*: A Composite Response", Journal of Bacteriology, 1970, vol. 103, No. 1, pp. 9-15.
Kondo, T. et al., "Rapid Degradation of Cdt1 Upon UV-Induced DNA Damage Is Mediated by $SCF^{SkP2}$ Complex", The Journal of Biological Chemistry, 2004, vol. 279, No. 26, pp. 27315-27319.
Webster's Dictionary, "Particle" disclosure, downloaded from the world wide web on May 26, 2006.
Blosse, P.T., et al., "Diminutive Bacteria Implications for Sterile Filtration" downloaded from the world wide web on May 26, 2006 from www.pall.com/34445_3813.asp.
Bottiglieri, P., Derwent Document Identifier: CH 678489A, "Cosmetic compsn. contg. placental extract, thymus", Sep. 30, 1991.
English Abstract for Publication No. 2001261522.
Abstracts of Japan 05009107, Jan. 19, 1993.
Asker et al. "Effect of Ultraviolet Light on the Release of Theophylline from Ethylcellulose-Based Sustained-Release Microcapsules." *PDA Journal of Pharmaceutical Science & Technology* May-Jun. 1997 vol. 51, No. 3, pp. 125-129.

(Continued)

*Primary Examiner* — Michael G Hartley
*Assistant Examiner* — Robert Cabral
(74) *Attorney, Agent, or Firm* — Drinker Biddle & Reath LLP

(57) ABSTRACT

The invention relates mainly to a particle comprising at least one biopolymer which is degradable under the effect of an electromagnetic wavelength, notably the wavelength of which is in the spectrum of the wavelengths emitted by the sun, this biopolymer comprising nucleosides. The invention also relates to compositions containing such particles with the aim of delivering an active principle.

These particles can be used mainly in cosmetics, in dermatology, in pharmacy, in agri-food or en agro-industrials.

27 Claims, 2 Drawing Sheets

(56) References Cited

OTHER PUBLICATIONS

Dobrov et al. "UV laser induced RNA-protein crosslinks and RNA chain breaks in Tobacco mosaic virus RNA in situ." *Photochem Photobiol* May 1989 vol. 49, No. 5, pp. 595-598. (Abstract Only).
Vail, N.; Dixon, H. Proceedings—28th International Symposium on Controlled Release of Bioactive Materials and 4th Consumer & Diversified Products Conference, San Diego, CA, Jun. 23-27, 2001, vol. 1, 108-109.
English abstract for Cesarini et al. Soleil et environnement. *Nouv Dermatol*, vol. 21, Supple. 2, pp. 30-36 (2002).
Palmieri et al. "Short communication, Gastro-resistant microspheres containing keteprofen". *Journal Microencapsulation*, vol. 19, No. 1, pp. 111-119 (2002).
Lorenzo-Lamosa et al. "Development of a microencapsulatd form of cefuroxime axetil using pH-sensitive acrylic polymers". *Journal Microencapsulation*, vol. 14, No. 5, pp. 604-616 (1997).
Ramkissoon-Ganorkar et al. "Modulating insulin-release profile from pH/theremosensitive polymeric beads through polymer molecular weight". *Journal of Controlled Release*, vol. 59, pp. 287-298 (1999).
Ichikawa et al. "A novel positively thermosensitive controlled-release microcapsule with membrane of nano-sized poly (N-isoproplyacrylamide gel dispersed in ethylecellulose matrix". *Journal of Controlled Release*, vol. 63, pp. 107-119 (2000).
Vyas et al. "Inhibition of glyceraldehydes-3-phosphate dehydrogenase in tissues of the rat by acrylamide and related compounds". *Neuro Toxicology*, vol. 6, No. 3, pp. 123-132 (1985).
Hayashi et al. "Cytoxic effects of acrylamide and its related compounds assessed by protein content, LDH activity and cumulative glucose consumption of neuron-rich cultures in a chemically defined medium". *Arch Toxicology*, vol. 63, pp. 308-313 (1989).
Weadock et al. "Effect of physical crosslinking methods on collagen-fiber durability in proteolytic solutions". *Journal of Biomedical Materials Research*, vol. 32, pp. 221-226 (1996).
Lee et al. "Characterization of UV-irradiated dense/porous collagen membranes: morphology, enzymatic degradation, and mechanical properties". *Yonsei Medical Journal*, vol. 42, No. 2, pp. 172-179 (2001).

Murthy et al. ":Dissolution stability of hard-shell capsule products, Part I: The effect of exaggerated storage conditions". *Pharmaceutical Technology*, vol. 13, pp. 72-86 (1989).
Van Den Bulcke et al. "Structural and rheological properties of methacrylamide modified gelatin hydrogels". *Biomacromolecules*, vol. 1, pp. 31-38 (2000).
Geetha et al. Photo-oxidative degradation of polyethylene: Effect of polymer characteristics on chemical changes and mechanical properties. Part I—Quenched polyethylene. *Polymer Degradation and Stability*, vol. 19, pp. 279-292 (1987).
Getlichermann et al "Degradation of polymer blends: Part VII. Photo-oxidation in natural weathering conditions of polyethylene containing styrene-butadiene or styrene-isoprene copolymers". *Polymer Degradation and Stability*, vol. 43, pp. 343-352 (1994).
Mamda et al. "Photoinduced phase transition of gels". *Macromolecules*, vol. 23, pp. 1517-1519 (1990).
Suzuki et al. "Phase transition in polymer gels induced by visible light". *Letters to Nature*, vol. 346, pp. 345-347 (1990).
Qiu et al. "Environment-sensitive hydrogels for drug delivery". *Advanced Drug Delivery Review*, vol. 53, pp. 321-339 (2001).
Yui et al. "Photo-responsive degradation of heterogeneous hydrogels comprising crosslinked hyaluronic acid and lipid microspheres for temporal drug delivery". *Journal of Controlled Release*, vol. 26, pp. 141-145 (1993).
Asker et al. "Effect of ultraviolet light on the release of theophylline from ethylecellulose-based sustained-release microcapsules". *PDA Journal of Pharmaceutical Science and Technology*, vol. 51, No. 3, pp. 125-129 (1997).
Cesarini et al. Soleil et environnement. *Nouv Dermatol*, vol. 21, Supple. 2, pp. 30-36 (2002).
Dobrov et al. "UV laser induced RNA-protein crosslinks and RNA chain breaks in *Tobacco mosaic virus* RNA in situ". *Photochemistry and Photobiology*, vol. 49, No. 5, pp. 595-598 (1989).
Hanson et al. "Observation and quantification of ultraviolet-induced reactive oxygen species in Ex Vivo human skin". *Photochemistry and Photobiology*, vol. 76, No. 1, pp. 57-63 (2002).

* cited by examiner

PARTICLES COMPRISING A BIOPOLYMER WHICH IS DEGRADABLE UNDER THE EFFECT OF AN ELECTROMAGNETIC WAVE AS EMITTED BY A SOLAR RADIATION

CROSS-REFERENCE TO RELATED APPLICATION

This application is a continuation application of U.S. patent application Ser. No. 10/346,690, filed Jan. 15, 2003, which is claims priority to French Patent Application No. 02 16637, filed Dec. 24, 2002.

The invention relates mainly to a particle comprising at least one biopolymer which is degradable under the effect of an electromagnetic wave, notably the wavelength of which is in the spectrum of the wavelengths emitted by the sun, this biopolymer comprising nucleosides.

More particularly, the invention finds cosmetic, dermatological, pharmaceutical, agri-food or agro-industrial use, in releasing an active principle contained by this particle when it is subjected to an electromagnetic wave.

STATE OF THE ART

With the aim of better mastering the bioavailability and the release of a microencapsulated active, many studies have been made so as to develop microcapsules or microspheres which release their actives under the influence of physical factors such as pH or temperature.

For pharmaceutical applications, the use of pH-dependent polymers such as Eudragit® S and L (Bayer), cellulose acetate phthalate, cellulose acetate trimellitate and hydroxypropyl methyl cellulose phthalate has enabled the development of gastro-resistant microspheres which release a low amount of an active in an acid medium (0.1N HCl) but which have very rapid release kinetics after a sharp increase of the pH (towards 6-7) (Palmieri et al., 2002, J. Microencaps., 19, 1, 111-119; Lorenzo et al., 1997, J. Microencaps., 14, 5, 607-616). These polymers do in fact have the property of being insoluble at acidic pHs and dissolve only towards pHs neighboring 5 to 6. Thus, the microencapsulated active is not very much released in a gastric medium (which is very acidic), and this enables for example reducing the risks of irritation of the gastric mucosa, which phenomena are observed for many chemical compounds.

More recently, pieces of work on N-isopropylacrylamide, butyl methacrylate and acrylic acid have enabled developing microspheres which are both pH- and heat-sensitive (Ramkissoon-Ganorkar et al., 1999, J. Control. Release, 59, 287-298; Ichikawa et al., 2000, J. Control. Release, 63, 107-119). These techniques enable using the variations of pH and temperature in order to load the microsphere with active or in order to trigger off the release of the microencapsulated active. However, these compounds are highly toxic and this limits their uses in cosmetics (Vyas et al., 1985, Neurotoxicology, 6, 3, 123-132; Hayashi et al., 1989, Arch. Toxicol., 63, 4, 308-313).

Apart from the stimuli such as the pH or the temperature, it would seem particularly interesting to develop microspheres or microcapsules which release their actives under the action of light and/or ultra-violets (UV). The spheres or capsules thus obtained could in fact release anti-oxidants, solar filters or molecules enabling inducing a barrier effect, only when the skin really needs it, the encapsulation enabling avoiding the skin contact and penetration of certain actives which are particularly irritant, even allergenic (vitamin A, vitamin E, solar filters, perfumes, etc. . . . ). However, for many polymers which are commonly used in micro-encapsulation, ultra-violets cause a splitting and then an immediate rearrangement of their constituent chemical structures (radical photo-polymerization), thus leading to a cross-linking and then to the formation of polymers, which are sometimes even more resistant. This is the case notably with collagen (Weadock et al., 1996, J. Biomed. Mater. Res., 32, 2, 221-226; Lee et al., 2001, Yonsei Med. J., 42, 2, 172-179) or with certain derivatives of gelatin (Murthy et at, 1989, Pharm. Technol., 13, 72; Van Den Bulcke et at, 2000, Biomacromolecules, 1, 1, 31-38).

Some porymers are themselves degraded by light or ultra-vootets. This is the case with certain polyethylene films (Geetha et al., 1987, Polym. Deg. Stab., 19, 279-292) which can notably contain styrene-butadiene copolymers (Getlichermann et al., 1994, Polym. Deg. Stab., 43, 343-352). These films undergo a photo-oxidation, and then a fragmentation of their structures, under the action of solar radiation. Industrially, these products are used for coating agricultural fertilizers, with, as the effect sought after, a progressive release as a function of the solar exposure. However, the doses of solar energy which are necessary for the degradation of the film are very significant (500,000 ($kJ/m^2$), doses which correspond to more than 15 days of exposure In full Summer (Getlichermann et al., 1994, Polym. Deg. Stab., 43, 343-352) and which are therefore incompatible with the rapid degradation expected during a dally solar exposure (as an indication, the dairy soiar energy received varies from 5,000 to 10,000 $kJ/m^2$).

Certain derivatives of N-lsopropylacrylamlde can also acquire a very interesting reactivity to ultra-violets by grafting of a UV-photosensltlve molecule such as bis(4-dimethylamino)phenylmethyl leucocyanide (Mamada et at., 1990, Macromolecules, 23, 1517-1519). The ultra-violet light first of all creates an ionization reaction in the gel formed from this polymer, and this leads to an increase in the internal osmotic pressure and a swelling of the gel. In the absence of ultra-violet light, the equilibrium is reversed and the gel beaks up, it Is said that the gel "collapses".

In the same way, the grafting of chromophores-which are sensitive to light, such as, for example, the chlorophyllin-copper complex or its trisodium salts, onto N-lsopropylacrylamide polymers enables obtaining gels which are reactive to visible light (Suzuki et al., 1990, Nature, 1990, 346, 26, 345-347; Qiu et al., 2001, Adv. Drug. Deliv. Rev., 53, 321-339).

When the light is applied onto the hydrogen the chromophore absorbs the solar energy to locally transform it into heat, in thus increasing the temperature of the gel. As the gels obtained are also heat-sensitive, the increase in the temperature thus leads to a contraction of the gel. The use of these gels in microspheres could enable a release of the active at the moment at which the gel contracts . . . .

However, a high toxicity of the molecules formed from the isopropylacrylamide does not facilitate the use of this technique in cosmetics (Vyas et al., 1985, Neurotoxicology, 6, 3, 123-132; Hayashi et al., 1989, Arch. Toxicol., 63, 4, 308-313).

Few pieces of work describe the use of natural polymers for preparing microspheres or microcapsules having properties of release of the active encapsulated under UV irradiation or light.

With this in mind, Yui's group (Yui et al., 1993, J. Controlled Release, 26, 141-145) proposed the use of a gel of hyaluronic acid coupled to a photosensitizer, methylene blue, as support medium of the microspheres. Under the effect of the light, there is a production of $OH°$ radicals which depolymerize and fluidify the hyaluronic acid gel, and thus enable the degradation of the spheres and the release of the active principles.

Pieces of work by Asker et al. (Asker et al., 1997, PDA J Pharm Sci Technol., 51, 3, 125-129) have shown that microcapsules made from ethyl cellulose were particularly degraded under ultra-violets. However, it was necessary to irradiate the samples for 7 days and under wavelengths of 230-270 nm (UVC). Now, UVCs, which are very strong energy radiations which do not meet the earth's surface very much (Cesarini, 2002, Nouv. Dermatol., 21, 2, 30-36). The experimental conditions selected are thus quite far from the realistic conditions of use in the case of a cosmetic application.

Very few publications exist in relation to the development of microspheres or microcapsules which deliver their actives after solar and/or UV irradiation. Either the products developed react only with radiations which do not approach very much the solar spectrum received on earth (UVC for example), or the amounts of energy necessary for the degradation of the polymer are too significant to envisage a rapid mechanism of action in case of daily use, and notably in case of a cosmetic, dermatological, pharmaceutical, agri-food or agro-industrial use. Moreover, the toxicity of all the photoreactive polymers obtained by organic synthesis hitherto remains a brake for their cosmetic use.

AIMS OF THE INVENTION

A main aim of the invention is to solve the novel technical problem consisting of providing particles which are formed from natural biopolymers, which can deliver active principles which are optionally contained by these particles, under the action of an electromagnetic wave, notably the wavelength of which is in the spectrum of the wavelengths emitted by the sun.

Another aim of the invention is to solve the novel technical problem consisting of providing such particles which contain an active principle which is active in the field of cosmetics, dermatology, pharmacy, agri-food or agro-industry.

Another main aim of the invention is to solve the novel technical problem consisting of providing a cosmetic, dermatological, pharmaceutical, agri-food or agro-industrial composition, comprising at least one particle as defined above.

Another aim of the invention is to solve the technical problem consisting of providing a solution enabling releasing an active principle in relation with the exposure to an electromagnetic wave, notably the wavelength of which corresponds to that emitted by the sun.

DESCRIPTION OF THE INVENTION

Thus, the present invention describes a technique for obtaining particles which are formed from natural biopolymers which can deliver their actives (cosmetic, dermatological, pharmaceutical, agri-foods or agro-industrial actives) under the action of light, and this at doses which are more compatible with a moderate exposure of the order of a day, even a dose of a few hours for cosmetic applications for example.

The microspheres or microcapsules, nanospheres and nanocapsules, liposomes, which are described in the present invention, are made by the use of deoxyribonucleic acid (DNA), ribonucleic acid (RNA), of oligonucleotides or of oligonucleosides. These compounds are in fact classically known for their sensitivity to UV radiation, a sensitivity which can induce, in vivo, mutations of the genes carried by these structures within the chromosomes for example.

Thus, in the presence of UV radiation and of oxygen, there is a production of free radicals which cleave, at numerous locations, DNA molecules, oligonucleotides, as well as RNA molecules (Dobrov et al., 1989, Photochem. Photobiol., 49, 5, 595-598). The inventors had the idea of using this property which is generally considered to be negative and as being harmful to the integrity of the chromosomal property of the cells, as a beneficial property within the context of the invention, the DNA, RNA molecules, the oligonucleotides and oligonucleosides thus being used as polymers for constituting the membranes of the spheres or of the liposomes thus formed.

Thus, under solar irradiation and more particularly under UV, the free radicals formed (Hanson et al., 2002, Photochem. Photobiol., 76, 1, 57-63) <<hydrolyze>> the DNA, RNA molecules, the oligonucleotides or the oligonucleosides which constitute the membrane of the sphere, of the capsule or of the liposome. Thus, in proportion to the dose of the radiation received, there is a production of free radicals for example on the skin, which progressively cause a local rupture of the membrane of the sphere, of the capsule or of the liposome, and thus enable releasing the active.

According to a first aspect, the invention relates to a particle comprising at least one biopolymer which is degradable under the effect of an electromagnetic wave, notably the wavelength of which is in the spectrum of the wavelengths emitted by the sun, this biopolymer comprising nucleosides.

Advantageously, the biopolymer is selected from the group consisting of a DNA, an RNA, an oligonucleotide, an oligonucleoside, or one of a mixture of these.

Advantageously, the biopolymer is selected from the group consisting of DNA of marine origin, RNA of marine origin, DNA of plant origin, RNA of plant origin, oligo-antisenses, polyamide nucleic acids (PNA), small interfering RNAs (siRNAs), messenger RNAs or mRNAs, hybrid molecules containing an oligonucleosidic and/or oligonucleotidic part, and oligonucleosides and oligonucleotides having chemical modifications such as graftings of hydrophobic molecules.

Advantageously, the particle is a microcapsule, a nanocapsule, a microsphere, a nanosphere, a liposome, or any mixture of these particles.

Advantageously, the size of the microcapsules or of the microspheres is between 1 and 100 μm, preferably between 2 and 80 μm.

Advantageously, the size of the nanocapsules or of the nanospheres is between 10 nm and less than 1 μm, preferably between 20 and 900 nm.

Advantageously the particle contains at least one active principle, which is preferably topically acceptable, and which can be released under the effect of a solar radiation and/or UV radiation.

The invention has the advantageous particularity that the release of the active principle is effected in relation with the intensity of the energy of the radiation.

Very advantageously, the invention notably enables the release of a sufficient amount of the active principle in a period of about 24 hours after exposure to a radiation of energy sufficient to cause such a release.

Advantageously, the release of a sufficient amount of the active principle is effected during an exposure to a radiation of energy greater than 200 kJ/m2, preferably greater than 4,000 kJ/m2.

The invention is notably particularly pertinent for encapsulating a liposoluble or hydrosoluble active principle.

Advantageously, the active principle is selected from the group consisting of antioxidants, moisturizing agents, solar filters, perfumes, vitamins, co-enzymes, anti-bacterial agents and preservatives, moisturizing actives, <<anti-age>> actives, skin barrier tonics namely helping to restore the skin barrier, active principles which protect from a solar radiation and/or UV radiation, active principles which repair the skin during or after an exposure to a solar radiation and/or UV radiation, as well as any active principle the progressive release of which is necessary to control by linking it to the dose of radiation, and notably of UV, applied, active principles which are badly absorbed by the skin, and one of a mixture of these.

The mixture of various active principles having or not having a synergistic effect notably enables realizing a combined and/or intensified action.

The invention can notably be realized by cross-linking, notably by interfacial polymerization, with a cross-linking agent notably selected from the group consisting of dichlorides of organic acids such as fumaric acid, sebacic acid, azelaic acid, terephthalic acid phthalic acid, succinic acid, glutaric acid, adipic acid, dichlorides of tricarboxylic acids, such as citric acid, trichlorides of tricarboxilic acids, such as citric acid, acid dianhydrides, diisocyanates, dialdehydes such as glutaraldehyde and formaldehyde, and di-epoxides.

According to a second aspect, the invention relates to a cosmetic, dermatological, pharmaceutical, or agri-food composition comprising at least one particle, as defined above, or one of the various possible mixtures of these particles.

Advantageously, this composition further comprises an excipient, such as an agent selected from the group consisting of preservatives, gelling agents, which are hydrophilic or lipophilic, solvents, emulsifiers, co-emulsifiers, moisteners, thickeners, stabilizers, antioxidants, solar filters, pigments, colorant materials, organic or inorganic fillers, perfumes, and odor absorbers.

Advantageously, this composition is formulated in a form which is acceptable cosmetically, dermatologically, pharmaceutically, for agri-food or agro-industrially, notably in a form selected from the group consisting of a solution, which is aqueous or oily, a cream or an aqueous gel or an oily gel, notably in a pot or in a tube, notably a shower gel, a shampoo; a milk; an emulsion, a microemulsion or a nanoemulsion, which is notably oil-in-water or water-in-oil or multiple or silicone-containing; a lotion, notably in a glass bottle, a plastic bottle, a measure bottle, an aerosol, or in a spray; an ampoule; a liquid soap; a dermatological bar; an ointment; a foam; and an anhydrous product, preferably which is liquid, pasty or solid, e.g. in a form of a stick, notably in a form of lipstick.

According to a third aspect, the invention relates to the use of particles as defined above, or of a composition as defined above, for releasing an active, during an exposure of the particles to an electromagnetic wave, notably the wavelength of which is in the spectrum of the wavelengths emitted by the sun, notably in relation with the intensity of the energy of the electromagnetic wave.

Advantageously, these particles or compositions are used for protecting or repairing the skin during or after an exposure to such electromagnetic waves, notably to a solar and/or UV radiation.

Thus, the active is rapidly released at the same moment as when the skin needs it.

These particles or compositions can also be used advantageously for releasing, according to the intensity of the energy of the radiation, an active principle, which is either badly tolerated by the skin, or which would penetrate too rapidly into the skin, such as a solar filter, notably with the aim of releasing this active only in case of need.

The invention can in fact be used for slowing down to the maximum the penetration of an active that is known to be very rapidly absorbed or is badly "tolerated" by the skin, such as a solar filter for example. From this fact, this active will be released only in case of real need, i.e. notably in case of a prolonged solar exposure.

The invention can also be used progressively releasing an active throughout the day, either with a view to improving its release throughout the whole day, e.g. with a view to the progressive release of an anti-oxidant for protecting the skin, of a substance enabling the reconstruction of the skin barrier for a progressive reconstruction, of a perfume for a release throughout the whole day, of UV filters for a progressive protection against UVs, of moisturizing active principles for a long term moisturization, of anti-age actives for a release throughout the whole day, of anti-microbial agents or of preservatives for anti-microbial effects arising progressively throughout the whole day, etc. . . . From this fact, these actives encapsulated in such particles will be released only in case of real need, i.e. notably in case of a prolonged solar exposure.

The invention finds a cosmetic, dermatological or pharmaceutical use essentially by application of these particles or compositions via the topical route on a living being, notably on a human being or on an animal. From this fact, the invention can very advantageously be implemented by incorporating, within the particles, active principles enabling protecting or repairing the skin of a subject in a controlled manner as a function of the solar exposure.

A agri-food or agro-industrial use of these particles or compositions notably by application around a seed, on the leaves of a plant, on the entire plant, on a part of the plant, on the base of the plant, on the roots of the plant, or around the plant, can advantageously be found in releasing an active principle said seed or plant of which would be in need thereof, or for providing an indication of a need of said seed or plant (fertilizer, pesticide, herbicide, for example).

According to a fourth aspect, the invention relates to a method of cosmetic care, characterised in that particles as defined above, or a composition as defined above, containing at least one cosmetic active principle, is/are applied on the skin, and/or on the body hairs, and/or on the hair, and in that the particles, which are alone or in a mixture so as to form a cosmetic composition, degrade during an exposure to the sun, and release at least one active principle, thus enabling providing an indication of the effects of the sun on the skin, and/or on the body hairs, and/or on the hair, and/or providing a beneficial effect to the skin, and/or to the body hairs and/or to the hair, during an exposure to the sun.

According to a fifth aspect, the invention relates to a method of treatment of a plant, characterised in that particles, as defined above, or a composition as defined above, containing at least one food active principle, is/are applied around the seed, on the leaves of a plant, on the entire plant, on a part of the plant, on the base of the plant, on the roots of the plant, or around the plant, and in that the particles, which are alone or in a mixture so as to form a agri-food composition, degrade during an exposure to the sun, and thus release at least one active principle enabling providing an indication to the plant of the effects of the sun and/or treating at least one harmful effect linked to an exposure to the sun and/or improving the benefits linked to an exposure to the sun.

In the present invention, by <<an electromagnetic wave>>, the inventors mean a whole of electromagnetic waves which are able or not to have the same wavelength.

Within the context of the present invention, the wavelengths emitted by the sun are notably comprised as being the electromagnetic wavelengths which correspond to the range of infra-red, but more particularly ultraviolet waves (UV), which roughly corresponds to but in no way are limited to, wavelengths of between $10^{-8}$ and $4.10^{-7}$ m and visible waves, which also roughly correspond to, but are in no way limited to, wavelengths of between 400 and 800 nm.

The Figures annexed enable visualizing the effect of an electromagnetic wave firstly on the product of the invention and secondly on a control product.

On the Figures:

FIG. 1 is a microscopic view of microspheres prepared according to the invention (magnification ×20). This microscopic view is made before carrying out an irradiation;

FIG. 2 corresponds to the microspheres according to the invention, which is observed after irradiation under solar light (solar irradiator) at a dose of 3,800 kJ/m². This microscopic view enables observing the degradation of the microspheres according to the invention;

FIG. 4 enables observing that there is no degradation of the microspheres.

Figure 1:
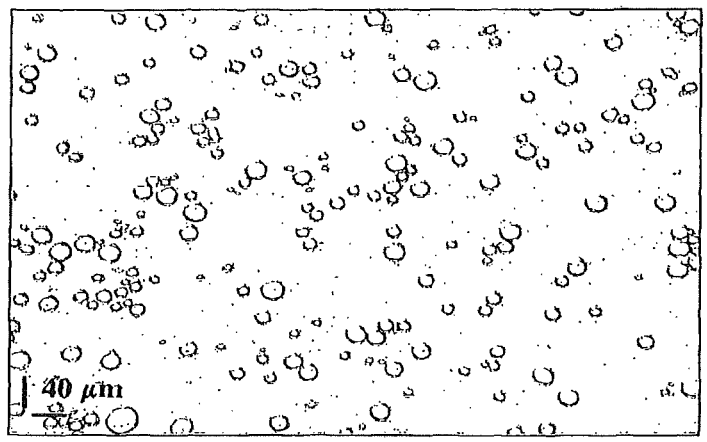
Figure 2:
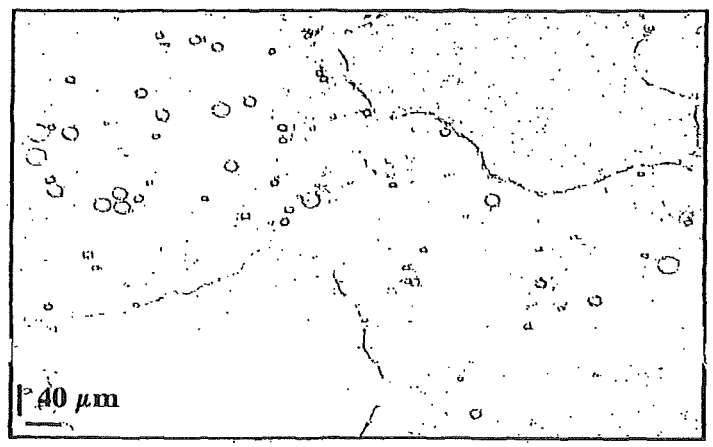

The composition of the invention used for making FIGS. 1 and 2 corresponds to a preparation made according to Example 1.

Figure 3:
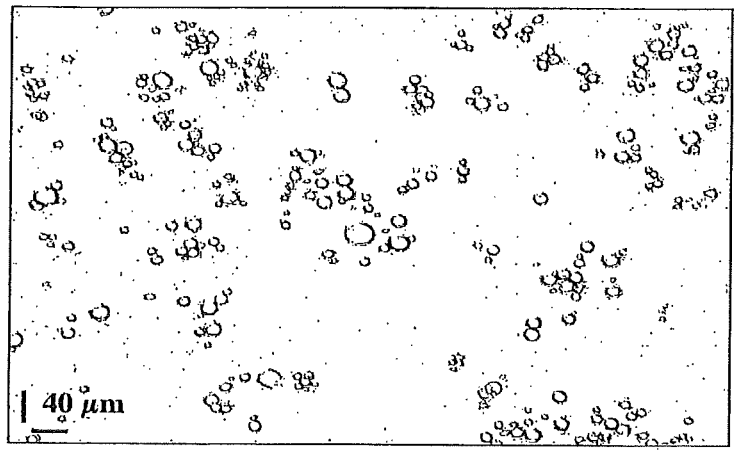
FIG. 3 represents a microscopic view (magnification ×20) of microspheres prepared according to a prior art technique and have been prepared according to the method of Example 3.
Figure 4:
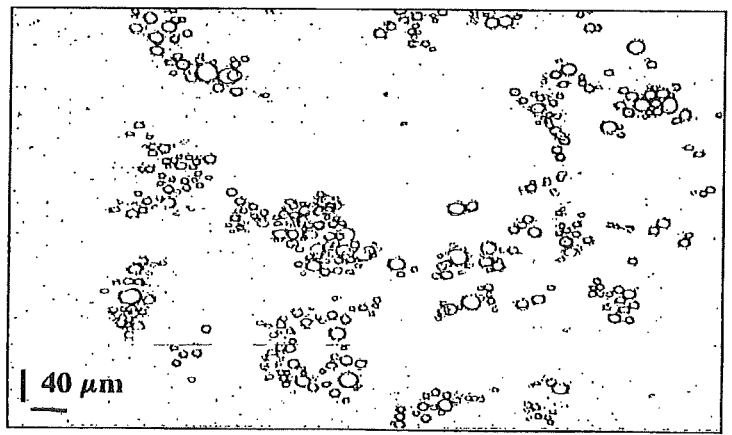
FIG. 4 represents the microspheres observed in FIG. 3 after irradiation under solar light (solar irradiator) at a dose of 3,800 kJ/m².

The control composition used for making FIGS. 3 and 4 corresponds to a preparation made according to Example 3.

Other aims, characteristics and advantages of the invention will appear clearly to the person skilled in the art upon reading the explanatory description which makes reference to the Examples which are given simply as an illustration and which in no way limit the scope of the invention.

The Examples make up an integral part of the present invention, and any characteristic which appears novel with respect to any prior state of the art from the description taken in its entirety, including the Examples, makes up an integral part of the invention in its function and in its generality.

Thus, every example has a general scope.

Furthermore, in the Examples, all percentages are given by weight, unless indicated otherwise, temperature is expressed in degrees Celsius unless indicated otherwise, and the pressure is atmospheric pressure, unless indicated otherwise.

EXAMPLES

Example 1

Method of Preparation of Microcapsules Based on Marine DNA a) A solution (1 kg) containing 4.8% (w/w) of sodium carbonate and 0.4% (w/w) of methyl paraben is prepared in pure laboratory water. Under mechanical agitation, 2% (w/w) of DNA of high molecular weight (extract of fish milt) is added. The agitation is maintained until a clear gel is obtained.

b) 9.6 ml of sebacoyl chloride are added to 320 g of caprylic/capric triglycerides oil (oily base). The whole is poured into 960 g of DNA gel under strong agitation made by an Ultra Turax® (IKA) type apparatus. A mechanical agitation is then maintained for 45 minutes.

c) The spheres are then separated from the reaction medium by centrifugation (3,800 rpm for 5 minutes).

d) Several washings with water are carried out so as to remove the excess of DNA gel which has not reacted as well as sodium sebacate.

e) The microcapsules recovered have a size of between 2 and 80 µm in diameter; they are then optionally placed in suspension in a gel (hydrophilic, lipophilic, or silicone type) optionally containing preservatives, which can be used in any cosmetic or pharmaceutical preparation. These microcapsules can also be dried (by atomization for example) and then sterilized by radiation, in order to be used in any type of application wherein the dry forms might be preferred (use in oily or silicone solutions for example).

Example 2

Method of Preparation of Microspheres Based on Marine DNA a) A solution (1 kg) containing 4.8% (w/w) of sodium carbonate and 0.4% (w/w) of methyl paraben is prepared in pure laboratory water. Under mechanical agitation, 2% (w/w) of DNA of high molecular weight (fish extract) is added. The agitation is maintained until a clear gel is obtained.

b) 144 g of terephthalic acid dichloride are dispersed in 3,600 g of caprylic/capric triglycerides oil.

c) In a cell, 54 g of sorbitan trioleate (Span 85, ICI) are dispersed in 2,700 g of caprylic/capric triglycerides oil.

d) 900 g of DNA gel prepared in a) are then placed in the cell under mechanical agitation. The solution prepared in b) is then added to the whole under mechanical agitation and the whole is agitated for 10 minutes by an Ultra Turax® (IKA) type agitator system. A reduced mechanical agitation is then maintained for 20 additional minutes.

e) The spheres obtained, of a size of 5 to 80 µm, are then separated from the reaction medium by centrifugation (2,000 rpm for 3 minutes).

f) Several washings with triglycerides oil are then carried out so as to eliminate the excess of acid dichloride.

g) The microcapsules recovered are then optionally placed in suspension in a gel (hydrophilic, lipophilic, or silicone type) containing or not containing preservatives, which can be used in any cosmetic or pharmaceutical preparation. These microcapsules can also be dried (by atomization for example) and then sterilized by radiation, in order to be used in any type of application wherein the dry forms might be preferred (use in oily or silicone solutions for example).

Example 3

Sensitivity to Solar Irradiation of Various Polymers

Various polymers, which are used classically in cosmetics for microencapsulation, were used for preparing the control microcapsules, according to the protocol described in Example 1. Thus, for example, microspheres were made from collagen and glycosaminoglycans according to the patent FR 2,642,329 (U.S. Pat. No. 5,395,620) (COLETICA), from plant proteins from wheat or from lupin according to the patent FR 2,766,090 (U.S. Pat. No. 5,912,016) (COLETICA), or from polysaccharides such as acacia according to the patent FR 2,688,422 (U.S. Pat. No. 5,562,924) (COLETICA).

A liposoluble colorant, having an absorption peak at 582 nm, was introduced in the oily phase.

The microspheres prepared in Example 1, as well as those prepared with the various polymers described above, are diluted to 25% (w/w) in a carbomer gel. 87.5 g of pure laboratory water containing 0.5% of sodium tricitrate are then added to 12.5 g of the gel thus obtained. The pH of the suspension of spheres thus obtained is adjusted to 5 with 1N HCl. 0.5 ml of this suspension are thus deposited in a pyrex hydrolysis tube. The tubes are then placed, laid down, in a solar irradiator (Suntest CP+, Atlas) reproducing the solar light spectrum. After irradiation, 3.5 ml of pure laboratory water, and then 2 ml of an organic solvent, isobutyl methyl ketone are added to each tube. Each test is then vortexed for 30 seconds at 2,000 rpm. The oil which is non-encapsulated or released under irradiation is then extracted in the organic phase and a reading of the optical density (OD) at 582 nm is then made. The greater the amount of oil released, the higher the OD is. By subtraction with the value of OD obtained for a non-irradiated sample and in comparing this value to the maximum OD being able to be obtained for a complete hydrolysis of the spheres, the percentage opening of the spheres under solar radiation is thus obtained which corresponds to the amount of oil released.

The solar irradiator used, by virtue of its xenon arc lamp, enables re-creating, the solar radiation the most accurately as possible (spectral range 300-3,000 nm).

Table 1 gives the average daily irradiations received at various points of the earth's globe (energy measured between 300 and 800 nm).

Moreover, so as to quantify in real terms the amount of energy received by the samples, we use either a solar radiometer (Sunstest CP+, Atlas) which measures the energy received between 300 and 800 nm, or a UV radiometer (VLX 3W, Fisher) specifically measuring the UVAs (peak at 365 nm) or UVBs (peak at 312 nm).

TABLE 1

Solar energies received per day at various regions of the earth's globe

| Region | Average energy delivered between 300 and 800 nm (corresponds to what the solar irradiator measures) |
| --- | --- |
| Florida | 9,315 kJ/m$^2$/day |
| Arizona | 12,602 kJ/m$^2$/day |
| Central Europe | 5,616 kJ/m$^2$/day |
| Bandol region | 7,945 kJ/m$^2$/day |

The various microcapsules prepared received a solar irradiation of 3,804 kJ/m$^2$ and then the percentage opening under solar irradiation was calculated.

The results obtained are presented in Table 2.

TABLE 2

Percentage opening under irradiation of 3,804 kJ/m$^2$ as a function of the type of polymer used for the preparation of the microcapsule

| Nature of the polymer | % opening |
| --- | --- |
| Polysaccharides and proteins extracted from acacia | 6.8 +/− 3.1 |
| Polysaccharides and proteins extracted from lupin | 12.4 +/− 7.4 |
| Wheat proteins | 0 +/− 1.7 |
| Collagen and glycosaminoglycans extracted from fish | 8.6 +/− 2 |
| DNA extracted from fish | 37.6 +/− 5.5 |

The microcapsules prepared from DNA, i.e. according to Example 1, have the most opening under solar irradiation.

Example 4

Study of the Influence of the on the Opening of the Microcapsules Prepared from Marine DNA The protocol followed is the same as that described in Example 3. The pH of the suspensions of spheres is adjusted to 5, 6, 7 or 8 before undergoing an irradiation at 2,000 kJ/m$^2$ and then the percentage opening under solar irradiation is calculated.

TABLE 3

Opening of the spheres as a function of the pH

| pH of the suspension of microcapsules prepared | % opening under irradiation of 2,400 kJ/m2 |
| --- | --- |
| 5 | 19.8 +/− 6.1 |
| 6 | 9.0 +/− 1.2 |
| 7 | 6.1 +/− 2.9 |
| 8 | 19.3 +/− 6 |

The opening of the spheres happens the most at pH 5 and at pH 8, but remains significant over all the range of cosmetic or dermopharmaceutical formulations.

Example 5

Evolution of the Opening of the Spheres as a Function of the Dose of Energy Received Three types of microcapsules were prepared from collagen and marine glycosaminoglycans, from a mixture of polysaccharides and plant proteins extracted from acacia and from marine DNA according to the protocol described in Example 1.

The microcapsules were then irradiated at various doses and the amount of oil released was quantified according to the technique described in Example 3. The percentages opening obtained are given in Table 4.

TABLE 4

Percentages opening of various types of microcapsules as a function of several doses of solar energy

| | Irradiation 1,243 kJ/m2 | Irradiation 2,467 kJ/m2 | Irradiation 3,804 kJ/m2 | Irradiation 4,927 kJ/m2 |
| --- | --- | --- | --- | --- |
| Microcapsules based on marine collagen | 1.7 +/− 1.5 | 1.6 +/− 1.3 | 7.5 +/− 3.2 | 16.6 +/− 8.8 |
| Microcapsules based on polysaccharides and proteins extracted from acacia gum | 0 +/− 0.6 | 0.3 +/− 2.7 | 3.5 +/− 1.5 | 6.7 +/− 3.4 |

TABLE 4-continued

Percentages opening of various types of microcapsules as a function of several doses of solar energy

| | Irradiation 1,243 kJ/m2 | Irradiation 2,467 kJ/m2 | Irradiation 3,804 kJ/m2 | Irradiation 4,927 kJ/m2 |
|---|---|---|---|---|
| Microcapsules based on marine DNA | 11.9 +/− 4.5 | 18.3 +/− 3 | 29.7 +/− 5.8 | 79.9 +/− 0.1 |

The more the energy delivered, the more the opening of the spheres containing the marine DNA is. Furthermore, the standard deviation of the percentage opening between the microcapsules based on marine DNA and the other microcapsules increases the greater the irradiation energy is.

Example 6

Microscopic Observation of the Microcapsules after Solar Irradiation

The spheres based on DNA which were prepared according to Example 1, and control microspheres prepared from collagen and glycosaminoglycans according to Example 5, are irradiated under solar light (solar irradiator), at a dose of 2,800 kJ/m². The products of the invention (FIGS. 1 and 2) as well as the control microspheres (FIGS. 3 and 4) are observed before and after irradiation: it is observed that only the microspheres of the invention have a membrane which is degraded under the action of the UV, the membrane of the control microspheres being not at all degraded under the same conditions.

Example 7

Modification of the Size of the Microcapsules of the Invention

All is done in a manner identical to what is presented in Example 1. In step b) of Example 1, the emulsification step is carried out under a more or less rapid agitation, with agitators of mechanical agitator type of Rayneri type (0-8,000 rpm) or Ultraturrax type (up to 20,000 rpm) in the presence or not of emulsifying agents, and the size of the emulsion (thus of the microcapsules) can be fixed between 1 µm and 100 µm in a very precise manner. Otherwise, the other steps of Example 1 are kept identical.

Example 8

Modification of the Size of the Microspheres of the Invention

All is done in a manner identical to what is presented in Example 2. In step d) of Example 2, the emulsification step is carried out under a more or less rapid agitation, with agitators of mechanical agitator type of Rayneri type (0-8,000 rpm) or Ultraturrax type (up to 20,000 rpm) in the presence of an increasing amount of emulsifying agent of Span 85 (ICI) type, and the size of the emulsion (thus of the microspheres) can be fixed between 1 µm and 100 µm in a very precise manner. Otherwise, the other steps of Example 2 are kept identical.

Example 9

Preparation of Nanocapsules According to the Method of the Invention

All is done in a manner identical to what is presented in Example 1. In step b) of Example 1, the emulsification step is carried out with the aid of a commercial high pressure homogenizer (APV, Alpha-Laval, etc. . . . ), generally used in the homogenization of food products, in the presence or not of emulsifying agents. The homogenization pressure is between 800 bars and 3,000 bars. The size of the nanocapsules thus formed is between 50 nm (high pressures) and 900 nm (lower pressures). Otherwise, the other steps of Example 1 are kept identical.

Example 10

Preparation of Nanospheres According to the Method of the Invention

All is done in a manner identical to what is presented in Example 2. In step d) of Example 2, the emulsification step is carried out with the aid of a commercial high pressure homogenizer (APV, Alpha-Laval, etc. . . . ), generally used in the homogenization of food products, in the presence or not of emulsifying agents. The homogenization pressure is between 800 bars and 3,000 bars. The size of the nanocapsules thus formed is between 50 nm (high pressures) and 900 nm (lower pressures). Otherwise, the other steps of Example 2 are kept identical.

Example 11

Use of Marine RNA for Preparing the Products of the Invention

All is done in a manner identical to what is presented in Examples 1, 2, and 7 to 10, but RNA of marine origin, which is commercially available (Javenech, France) is used, in proportions which are identical to those used in Example 1, such as, for example, RNA extracted from fish milt. The particles obtained are sensitive to UVs and hydrolyze under solar irradiation.

Example 12

Use of Plant DNA or Plant RNA for Preparing the Products of the Invention

All is done in a manner identical to what is presented in Examples 1, 2, and 7 to 10, but DNA of plant origin or RNA of plant origin, which are commercially available (Inocosm) are used, in proportions which are identical to those used in Example 1.

The particles obtained are sensitive to UVs and hydrolyze under solar irradiation.

Example 13

Use of Oligonucleotides or Oligonucleosides for Preparing the Products of the Invention All is done in a manner identical to what is presented in Examples 1, 2, and 7 to 10, but oligonucleosides or oligonucleotides, which are prepared by chemical synthesis and which are available from companies which manufacture these nucleosides or these nucleotides to order, are used for preparing these particles, in proportions which are identical to those used in Example 1.

The particles obtained are of smaller size than the particles obtained in Example 1 (1 to 50 μm), and are sensitive to UVs and hydrolyze under solar irradiation.

Amongst the nucleotides or nucleosides which can be used in the invention, the following are cited: oligo-antisenses, polyamide nucleic acids (PNA), RNAs called Small Interfering RNA (siRNAs), mRNAs, hybrid molecules containing a oligonucleosides and oligonucleotides part, and oligonucleosides and oligonucleotides having chemical modifications such as graftings of hydrophobic molecules for example.

Example 14

Use of Various Cross-Linking Agents

All is done in a manner identical to what is presented in Examples 1, 2, 7 to 13, but the cross-linking agents used are selected from:
- dichlorides of organic acids such as fumaric acid, sebacic acid, azelaic acid, terephthalic acid, phthalic acid, succinic acid, glutaric acid, adipic acid, dichlorides of tricarboxylic acids, such as citric acid, trichlorides of tricarboxilic acid, such as citric acid, acid dianhydrides, diisocyanates
- dialdehydes such as glutaraldehyde, formaldehyde
- di-epoxides The particles obtained are sensitive to the UVs and hydrolyze under solar irradiation.

Example 15

Preparation of Particles of Liposome Type, which are Sensitive to UVs or to Solar Radiation 1) 50 g of soya phospholipids enriched with phosphatidyl choline (T60, Lipoid) are added to 500 ml of demineralized water and the agitation is maintained (500 rpm) at ambient temperature until complete dissolution of the phospholipid.
2) After complete dissolution (about 4 hours), a preparation prepared beforehand of 50 g of marine DNA dissolved in 400 g of demineralized water, is added to this solution;
3) The pH of the whole is brought to a cosmetically acceptable pH in a traditional manner, namely between 4 and 8 (more preferably between 5 and 7).
4) 0.5 g of vitamin E acetate is introduced slowly under very strong agitation (10,000 rpm), and the agitation is maintained until complete homogeneity of the product obtained (about 30 minutes to 7 hours), if possible in reducing the speed of agitation to 500 rpm after a certain amount of agitation time. The whole can be carried out at a temperature of between 20 and 80° C., at a pressure of between an atmospheric pressure and 3,500 bars.
5) The product obtained, in the presence or not of DNA, is irradiated or not irradiated under UV or under solar light, as described in Example 3, and the amount of vitamin E acetate released is evaluated.

|  | Liposomes without DNA | Liposomes with DNA |
|---|---|---|
| Release without UV | 2% | 1% |
| Release under solar spectrum irradiation 3,500 J/m$^2$ | 4% | 35% |

There is therefore indeed a release of active principles when DNA, sensitive to UVs and solar radiation, is used for making the membrane of the liposomes.

Example 16

Use of Marine RNA for Preparing the Products of the Invention

All is done in a manner identical to what is presented in Example 15, but RNA of marine origin, which is commercially available, is used in amounts which are identical to those used in Example 15.

The particles obtained (liposomes) are sensitive to UV and hydrolyze under solar irradiation.

Encapsulated in these liposomes, an anti-oxidant such as tocopherol is released progressively under UV irradiation (40% after 3 hours, 80% after 6 hours of irradiation) for a UV-adapted protection of the skin.

Example 17

Use of Plant DNA or Plant RNA for Preparing the Products of the Invention

All is done in a manner identical to what is presented in Example 15, but DNA of plant origin or RNA of plant origin, which are commercially available (Inocosm), are used in amounts which are identical to those used in Example 15.

The particles obtained (liposomes) are sensitive to UV and hydrolyze under solar irradiation.

Encapsulated in these liposomes, a solar filter such as Parsol MCX is released progressively under UV irradiation (60% after 3 hours, 96% after 6 hours of irradiation) for a UV-adapted protection of the skin.

Example 18

Use of Oligonucleotides or Oligonucleosides for Preparing the Products of the Invention All is done in a manner identical to what is presented in Example 15, but oligonucleosides or oligonucleotides, which are prepared by chemical synthesis and which are available from companies which manufacture these nucleosides or these nucleotides to order, are used for preparing these particles, in proportions which are identical to those used in Example 15. The particles obtained (liposomes) are sensitive to UVs and hydrolyze under solar irradiation.

Amongst the nucleotides or nucleosides which can be used in the invention, the following are cited: oligo-antisenses, polyamide nucleic acids (PNA), RNAs called Small Interfering RNA (siRNAs), mRNAs, hybrid molecules containing a oligonucleosides and oligonucleotides part, and oligonucleosides and oligonucleotides having chemical modifications such as graftings of hydrophobic molecules for example.

Encapsulated in these liposomes, a commercial perfume (Dragoco) is released progressively under UV irradiation (odor always perceptible as from UV irradiation even 6 hours after a mono-application), for a UV-adapted release on the skin.

Example 19

Use of the Products of the Invention in Cosmetic or Pharmaceutical Formulations of Oil-in-Water Emulsion Type Formulation 19a:

| A | Water | qsp 100 |
|---|---|---|
|   | Butylene Glycol | 2 |
|   | Glycerol | 3 |
|   | Sodium Dihydroxycetyl Phosphate, Isopropyl Hydroxycetyl Ether | 2 |
| B | Glycol Stearate SE | 14 |
|   | Triisononaoin | 5 |
|   | Octyl Cocoate | 6 |
| C | Butylene Glycol, Methylparaben, Ethylparaben, Propylparaben, pH adjusted to 5.5 | 2 |
| D | Products of the invention | 0.01-10% |

Formulation 19b:

| A | Water | qsp 100 |
|---|---|---|
|   | Butylene Glycol | 2 |
|   | Glycerol | 3 |
|   | Polyacrylamide, Isoparaffin, Laureth-7 | 2.8 |
| B | Butylene Glycol, Methylparaben, Ethylparaben, Propylparaben; | 2 |
|   | Phenoxyethanol, Methylparaben, Propylparaben, Butylparaben, Ethylparaben | 2 |
|   | Butylene Glycol | 0.5 |
| D | Products of the invention | 0.01-10% |

Formulation 19c:

| A | Carbomer | 0.50 |
|---|---|---|
|   | Propylene Glycol | 3 |
|   | Glycerol | 5 |
|   | Water | qsp 100 |
| B | Octyl Cocoate | 5 |
|   | Bisabolol | 0.30 |
|   | Dimethicone | 0.30 |
| C | Sodium Hydroxide | 1.60 |
| D | Phenoxyethanol, Methylparaben, Propylparaben, Butylparaben, Ethylparaben | 0.50 |
| E | Perfume | 0.30 |
| F | Products of the invention | 0.01-10% |

Example 20 of the Invention

Use of the Products of the Invention in a Formulation of Water-in-Oil Type

| A | PEG 30-dipolyhydroxystearate | 3 |
|---|---|---|
|   | Capric Triglycerides | 3 |
|   | Cetearyl Octanoate | 4 |
|   | Dibutyl Adipate | 3 |
|   | Grape Seed Oil | 1.5 |
|   | Jojoba Oil | 1.5 |
|   | Phenoxyethanol, Methylparaben, Propylparaben, Butylparaben, Ethylparaben | 0.5 |
| B | Glycerol | 3 |
|   | Butylene Glycol | 3 |
|   | Magnesium Sulfate | 0.5 |
|   | EDTA | 0.05 |
|   | Water | qsp 100 |
| C | Cyclomethicone | 1 |
|   | Dimethicone | 1 |
| D | Perfume | 0.3 |
| E | Products of the invention | 0.01-10% |

Example 21 of the Invention

Use of the Products of the Invention in a Formulation of Shampoo or Shower Gel Type

| A | Xanthan Gum | 0.8 |
|---|---|---|
|   | Water | qsp 100 |
| B | Butylene Glycol, Methylparaben, Ethylparaben, Propylparaben Phenoxyethanol, Methylparaben, Propylparaben, Butylparaben, Ethylparaben | 0.5 / 0.5 |
| C | Citric acid | 0.8 |
| D | Sodium Laureth Sulfate | 40.0 |
| E | Product of the invention | 0.01-10% |

Example 22 of the Invention

Use of the Products of the Invention in a Formulation of Lipstick Type and Other Anhydrous Products

| A | Mineral Wax | 17.0 |
|---|---|---|
|   | Isostearyl Isostearate | 31.5 |
|   | Propylene Glycol Dipelargonate | 2.6 |
|   | Propylene Glycol Isostearate | 1.7 |
|   | PEG 8 Beeswax | 3.0 |
|   | Hydrogenated Palm Kernel Oil Glycerides, Hydrogenated Palm Glycerides | 3.4 |
|   | Lanolin Oil | 3.4 |
|   | Sesame Oil | 1.7 |
|   | Cetyl Lactate | 1.7 |
|   | Mineral Oil, Lanolin Alcohol | 3.0 |
| B | Castor Oil | qsp 100 |
|   | Titanium Dioxide | 3.9 |
|   | CI 15850:1 | 0.616 |
|   | CI 45410:1 | 0.256 |
|   | CI 19140:1 | 0.048 |
|   | CI 77491 | 2.048 |
| C | Products of the invention | 0.01-5% |

Example 23 of the Invention

Use of the Products of the Invention in an Aqueous Gel Formulation (Eye Surrounds, Slimmers, Etc. . . . )

| A | Water | qsp 100 |
|---|---|---|
| | Carbomer | 0.5 |
| | Butylene Glycol | 15 |
| | Phenoxyethanol, Methylparaben, Propylparaben, Butylparaben, Ethylparaben | 0.5 |
| B | Products of the invention | 0.01-10% |

Example 24

Evaluation of the Cosmetic Acceptance of a Preparation Containing at Least One Product of the Invention Toxicology tests were carried out on the microcapsules obtained according to Example 1, diluted to 25% in a 0.4% carbomer gel. The tests comprised an evaluation of the primary skin and ocular irritation in the rabbit, a study of the absence of abnormal toxicity by single oral administration in the rat and a research of the sensitizing power in the guinea pig.

Furthermore, a study of sensitization on human volunteers was made after dilution of the microspheres to 5% in a 0.4% carbomer gel.

Evaluation of the Primary Irritation of the Skin in the Rabbit:

The preparation described above is applied without dilution at the dose of 0.5 ml on the skin of 3 rabbits according to the method recommended by the OECD directive in relation to the study of <<the acute irritant/corrosive effect on the skin>>.

The product is classed according to the criteria defined in the Decision of 1 Feb. 1982 published in the JORF (Journal of the French Republic) of 21 Feb. 1982.

The results of these tests enable concluding that the preparation tested is classed as non irritant for the skin.

Evaluation of the Ocular Irritation in the Rabbit:

The preparation described above was instilled pure and in one batch at the rate of 0.1 ml in the eye of three rabbits according to the method recommended by the OECD directive No. 405 of 24 Feb. 1987 in relation to the study of "the acute irritant/corrosive effect on the eyes".

Test on the Absence of Abnormal Toxicity by Single Oral Administration in the Rat:

The preparation described was administered in one batch orally at the dose of 5 g/Kg of body weight, to 5 male rats and 5 female rats according to a protocol inspired from the directive of the OECD No. 401 of 24 Feb. 1987 and adapted to cosmetic products.

The LD0 and LD50 are found to be greater than 5,000 mg/Kg. The preparation tested is therefore not classed amongst the preparations which are dangerous by ingestion.

Evaluation of the Skin Sensitization Potential in the Guinea Pig:

The preparation described is subjected to the maximization test described by Magnusson and Kligmann, a protocol which is in agreement with the directive line No. 406 of the OECD.

The preparation is classed as non-sensitizing by contact with the skin.

Evaluation of the Sensitizing Potential in the Healthy Volunteer:

The preparation described (dilution of the capsules to 5% in a carbomer gel) is subjected to the test of verification of the absence of allergenic potential on a panel of 100 healthy volunteers.

The product is applied under an occlusive patch for 24 hours, and is then re-applied under patch for 2 days for a total of 9 applications (induction phase). After a period of 2 weeks, other patches containing the product are applied onto the skin of the volunteers and are left in contact for 24 hours. The clinical signs of irritation and skin sensitization are evaluated 24, 48 and 72 hours after the removal of the patch (challenge phase).

Under these experimental conditions, the product tested was classed as non-sensitizing by contact with the skin. Studies led in parallel also enabled leading to the conclusions that the product of the invention was also non-photosensitizing and non-photo-toxic.

What is claimed is:

1. A cosmetic composition which comprises at least one particle which comprises a membrane which consists of a biopolymer cross-linked with a crosslinking agent, wherein the biopolymer is selected from the group consisting of DNA of a marine origin, RNA of a marine origin, DNA of plant origin, RNA of plant origin, and any combination thereof, and wherein said membrane is degradable under the effect of an electromagnetic wave, and wherein the particle is a component selected from the group consisting of: a microcapsule, a microsphere, a nanocapsule, a nanosphere, and any mixture of these components, and wherein the crosslinking agent is selected from the group consisting of dichlorides of organic acids, dichlorides of tricarboxylic acids, trichlorides of tricarboxilic acids, acid dianhydrides, diisocyanantes, dialdehydes, and di-epoxides.

2. The cosmetic composition of claim 1, wherein the wavelength of said electromagnetic wave is in the spectrum of the wavelengths emitted by the sun.

3. The cosmetic composition of claim 1, wherein the particle is a component selected from the group consisting of: a microcapsule, a microsphere, and any mixture of these components.

4. The cosmetic composition of claim 3, wherein the size of the particle is in the range of 1 to 100 μm.

5. The cosmetic composition of claim 3, wherein the size of the particle is in the range of 2 to 80 μm.

6. The cosmetic composition of claim 1, wherein the particle is a component selected from the group consisting of: a nanocapsule, a nanosphere, and any mixture of these particles.

7. The cosmetic composition of claim 6, wherein the size of the particle is in the range of 10 nm to 1 μm.

8. The cosmetic composition of claim 6, wherein the size of the particle is in the range of 20 to 900 nm.

9. The cosmetic composition of claim 1, which contains at least one active principle.

10. The cosmetic composition of claim 9, wherein the active principle can be released under the effect of an electromagnetic radiation.

11. The cosmetic composition of claim 10, wherein said radiation is selected from the group consisting of a solar radiation, and a UV radiation.

12. The cosmetic composition of claim 9, wherein said active principle is topically acceptable.

13. The cosmetic composition of claim 10, wherein the release of the active principle is effected in relation with the intensity of the energy of the radiation.

14. The cosmetic composition of claim 10, wherein a release of the active principle is effected in a period of about at the maximum 24 hours after exposure to a radiation of energy sufficient to cause such a release.

15. The cosmetic composition of claim 10, wherein a release of the active principle is effected during an exposure to a radiation of energy greater than 200 kJ/m2.

16. The cosmetic composition of claim 15, wherein said energy of the radiation is greater than 4,000 kJ/m2.

17. The cosmetic composition of claim 10, wherein said active principle is a component selected from the group consisting of: a liposoluble active principle, and a hydrosoluble active principle.

18. A method of cosmetic care, comprising applying a particle which comprises a membrane which consists of a biopolymer cross-linked with a crosslinking agent, wherein the biopolymer is selected from the group consisting of DNA of a marine origin, RNA of a marine origin, DNA of plant origin, RNA of plant origin, and any combination thereof, and wherein said membrane is degradable under the effect of an electromagnetic wave, and wherein the particle is a component selected from the group consisting of: a microcapsule, a microsphere, a nanocapsule, a nanosphere, and any mixture of these components; the particle containing at least one cosmetically active principle, onto the skin or the hair; wherein the particle, which is alone or in a mixture so as to form a cosmetic composition, degrades during an exposure to the sun, and releases the at least one cosmetically active principle, thus providing an indication of the effects of the sun on said area of the body, and providing a beneficial effect to said area of the body, during an exposure to the sun, and wherein the crosslinking agent is selected from the group consisting of dichlorides of organic acids, dichlorides of tricarboxylic acids, trichlorides of tricarboxilic acids, acid dianhydrides, diisocyanantes, dialdehydes, and di-expoxides.

19. The method of claim 18, wherein the hair is body hair.

20. The cosmetic composition of claim 1, wherein the DNA, RNA, or any combination thereof is cross-linked.

21. The cosmetic composition of claim 20, wherein the DNA, RNA, or any combination thereof is cross-linked by a dichloride.

22. The cosmetic composition of claim 1, which is obtained by interfacial polymerization of the DNA, RNA, oligonucleotide, oligonucleoside, or any combination thereof.

23. The cosmetic composition of claim 1, wherein the biopolymer is DNA of marine origin.

24. The cosmetic composition of claim 4, wherein the biopolymer is DNA of marine origin.

25. The cosmetic composition of claim 1, wherein the electromagnetic wave causes a local rupture of the membrane.

26. The cosmetic composition of claim 1, wherein said dichloride of organic acids is a dichloride of an organic acid selected from the group consisting of fumaric acid, sebacic acid, azelaic acid, terephthalic acid, phthalic acid, succinic acid, glutaric acid, and adipic acid.

27. The method of claim 18, wherein the particle is in a mixture so as to form a cosmetic composition.

* * * * *